United States Patent
Shin et al.

(10) Patent No.: US 12,300,018 B2
(45) Date of Patent: May 13, 2025

(54) BIOMETRIC DETECTION USING PHOTODETECTOR ARRAY

(71) Applicant: Google LLC, Mountain View, CA (US)

(72) Inventors: Dongeek Shin, Santa Clara, CA (US); Paul Joseph Silberschatz, San Francisco, CA (US)

(73) Assignee: Google LLC, Mountain View, CA (US)

( * ) Notice: Subject to any disclaimer, the term of this patent is extended or adjusted under 35 U.S.C. 154(b) by 444 days.

(21) Appl. No.: 17/305,990

(22) Filed: Jul. 19, 2021

(65) Prior Publication Data

US 2023/0020039 A1     Jan. 19, 2023

(51) Int. Cl.
    *G06V 40/13*        (2022.01)
    *A61B 5/00*        (2006.01)
    (Continued)

(52) U.S. Cl.
    CPC ...... *G06V 40/1318* (2022.01); *A61B 5/02416* (2013.01); *A61B 5/02438* (2013.01);
    (Continued)

(58) Field of Classification Search
    CPC .......... G06V 40/1318; G06V 40/1341; G06V 40/15; G06V 40/70; A61B 5/02416; A61B 5/6803; A61B 5/681; A61B 5/02438; A61B 5/1172; A61B 2562/066; G06F 1/163; G06F 21/32; G06F 2218/08; G04G 9/007; G04G 21/08
See application file for complete search history.

(56) References Cited

U.S. PATENT DOCUMENTS

| | | | |
|---|---|---|---|
| 2009/0207154 A1* | 8/2009 | Chino | G06F 1/3262 345/173 |
| 2010/0013790 A1* | 1/2010 | Ahn | G06F 3/044 345/174 |

(Continued)

FOREIGN PATENT DOCUMENTS

| | | |
|---|---|---|
| CN | 103034342 B | 11/2015 |
| CN | 204839492 U | 12/2015 |

(Continued)

OTHER PUBLICATIONS

Liu, "A Heart Rate Finger Ring and Its Smartphone APP Through Customized NFC", Rose-Hulman Institute of Technology, Rose-Hulman Scholar, Graduate Theses—Electrical and Computer Engineering, May 2015, 96 pages.

(Continued)

*Primary Examiner* — Amandeep Saini
*Assistant Examiner* — Daniella M. DiGuglielmo
(74) *Attorney, Agent, or Firm* — Brake Hughes Bellermann LLP

(57) ABSTRACT

A computing device, such as a wearable device, may include a light source and a photodetector array. The photodetector array may be used to determine a touch event of a user that occurs during a time interval. A subset of the plurality of photodetectors associated with the touch event may provide detection signals at each of a plurality of times within the time interval, which may be aggregated to obtain a time series of aggregated detection signals. Biometric data of the user may be generated, based on the time series of aggregated detection signals.

18 Claims, 12 Drawing Sheets

(51) Int. Cl.

| | | |
|---|---|---|
| *A61B 5/024* | (2006.01) | |
| *A61B 5/1172* | (2016.01) | |
| *G04G 9/00* | (2006.01) | |
| *G04G 21/08* | (2010.01) | |
| *G06F 1/16* | (2006.01) | |
| *G06F 21/32* | (2013.01) | |
| *G06V 40/10* | (2022.01) | |
| *G06V 40/12* | (2022.01) | |
| *G06V 40/70* | (2022.01) | |

(52) U.S. Cl.
CPC ............ *A61B 5/1172* (2013.01); *G04G 21/08* (2013.01); *G06F 1/163* (2013.01); *G06F 21/32* (2013.01); *G06V 40/1341* (2022.01); *G06V 40/15* (2022.01); *A61B 5/6803* (2013.01); *A61B 5/681* (2013.01); *A61B 2562/066* (2013.01); *G04G 9/007* (2013.01); *G06F 2218/08* (2023.01); *G06V 40/70* (2022.01)

(56) References Cited

U.S. PATENT DOCUMENTS

| | | | | |
|---|---|---|---|---|
| 2011/0084934 A1* | 4/2011 | Tsuzaki | ................ | G06F 3/0412 345/174 |
| 2012/0253153 A1* | 10/2012 | Trumble | ............ | A61B 5/14551 600/324 |
| 2015/0199061 A1 | 7/2015 | Kitada et al. | | |
| 2016/0117048 A1* | 4/2016 | Frame | ................... | G06F 1/3231 345/174 |
| 2016/0313883 A1* | 10/2016 | Zhang | ................ | G06F 3/04883 |
| 2017/0281026 A1* | 10/2017 | Nick | .................... | A61B 5/7445 |
| 2017/0332923 A1 | 11/2017 | Masuda et al. | | |
| 2018/0173343 A1* | 6/2018 | Pi | ............................ | G06F 3/041 |
| 2020/0305740 A1* | 10/2020 | Quan | ................. | A61B 5/02007 |
| 2021/0374223 A1 | 12/2021 | Tada et al. | | |
| 2022/0031182 A1 | 2/2022 | Kato et al. | | |

FOREIGN PATENT DOCUMENTS

| | | | | |
|---|---|---|---|---|
| WO | 2019207472 A1 | | 10/2019 | |
| WO | WO-2020170523 A1 | * | 8/2020 | ............. G06F 21/32 |
| WO | WO-2020213620 A1 | * | 10/2020 | ......... A61B 5/02433 |

OTHER PUBLICATIONS

International Search Report and Written Opinion for PCT Application No. PCT/US2022/073715, mailed on Nov. 8, 2022, 12 pages.

* cited by examiner

BIOMETRIC DETECTION USING PHOTODETECTOR ARRAY

TECHNICAL FIELD

This description relates to biometric detection.

BACKGROUND

Many devices and techniques exist for capturing user biometrics. For example, various biometric monitoring techniques utilize a light source and photodetector, such as a light-emitting diode (LED) and photodiode, at a skin surface of a user to measure volumetric changes of blood circulation of the user. For example, a photoplethysmography (PPG) sensor may be used to measure such volumetric changes to determine a heart rate, respiration rate, and other biometric factors.

SUMMARY

According to one general aspect, a computer program product is tangibly embodied on a non-transitory computer-readable storage medium. The computer program product comprises instructions that, when executed by at least one computing device, are configured to cause the at least one computing device to determine a touch event of a user that occurs during a time interval and at a photodetector array that includes a plurality of photodetectors, and determine a subset of the plurality of photodetectors associated with the touch event. The instructions, when executed by the at least one computing device, are further configured to cause the at least one computing device to aggregate detection signals from the subset of the plurality of photodetectors at each of a plurality of times within the time interval, to obtain a time series of aggregated detection signals, and generate biometric data of the user, based on the time series of aggregated detection signals.

According to another general aspect, a computer-implemented method includes determining a touch event of a user that occurs during a time interval and at a photodetector array that includes a plurality of photodetectors, and determining a subset of the plurality of photodetectors associated with the touch event. The method further includes aggregating detection signals from the subset of the plurality of photodetectors at each of a plurality of times within the time interval, to obtain a time series of aggregated detection signals, and generating biometric data of the user, based on the time series of aggregated detection signals.

According to another general aspect, a computing device includes a processor, a storage medium storing instructions, a body, and a light source coupled to the body and configured to generate light in a direction of a user while the computing device is being worn or held by the user. The computing device further includes a photodetector array including a plurality of photodetectors that is coupled to the body and configured to detect light of the light source reflected from the user. The instructions, when executed by the processor, cause the computing device to determine, from the light of the light source reflected from the user, a touch event of a user that occurs during a time interval and at the photodetector array, determine a subset of the plurality of photodetectors associated with the touch event, aggregate detection signals from the subset of the plurality of photodetectors at each of a plurality of times within the time interval, to obtain a time series of aggregated detection signals, and generate biometric data of the user, based on the time series of aggregated detection signals.

The details of one or more implementations are set forth in the accompanying drawings and the description below. Other features will be apparent from the description and drawings, and from the claims.

DETAILED DESCRIPTION

Figure 1:
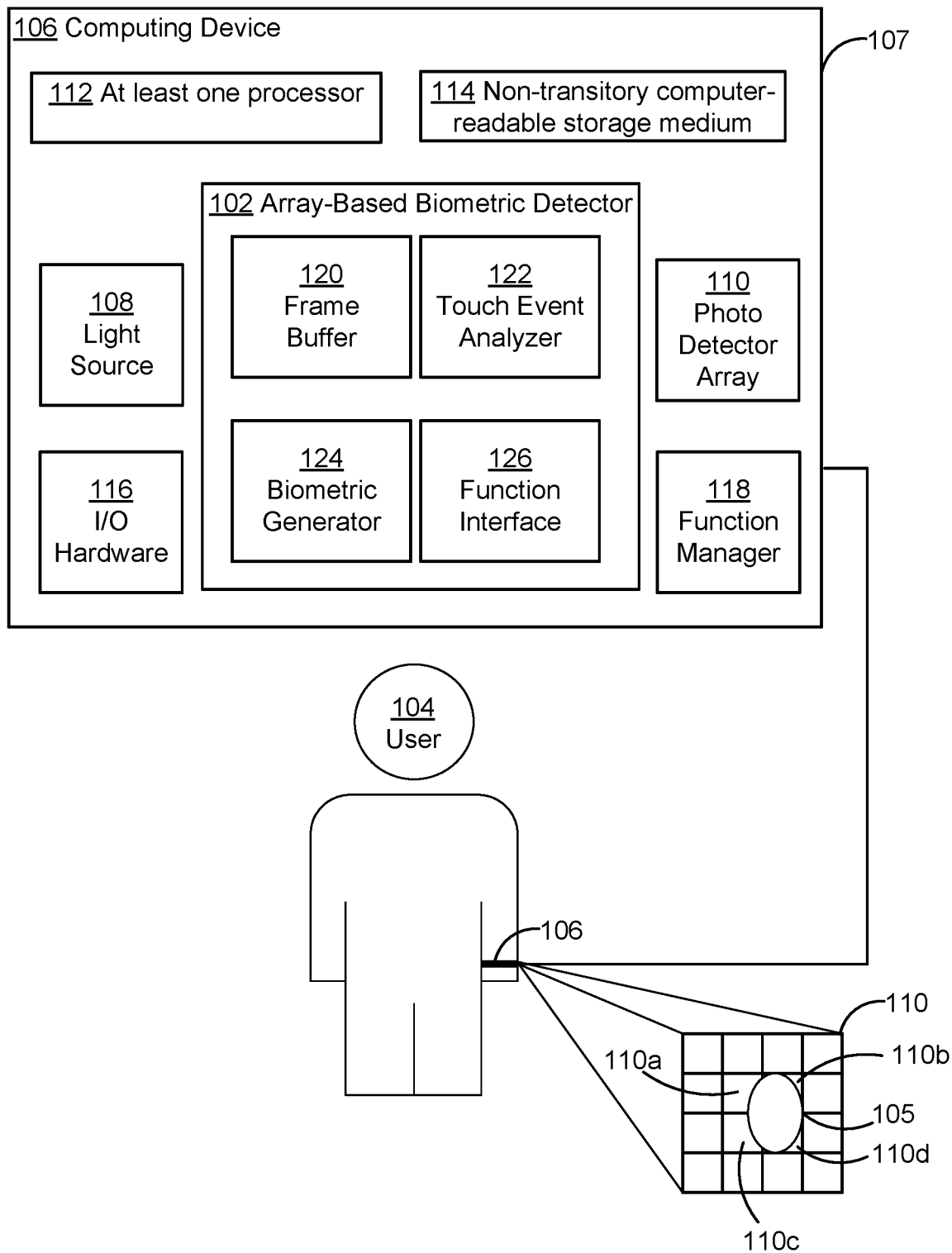
FIG. 1 is a block diagram of a system for biometric detection using a photodetector array.

Described systems and techniques enable biometric detection using a photodetector array. Rather than using a single photodetector, e.g., a single photodiode, the described systems use a plurality of photodetectors and associated detection techniques to generate biometric data such as, e.g., heart rate, heart rate variability, or respiration rate.

By using a plurality of photodetectors together with the described detection techniques, it is possible to collect various types of biometric data, even when a user contacts the photodetector array in different manners, or in any one of many different positions, and even when the user moves a point of contact (e.g., the user's finger) with respect to the photodetector array. Moreover, it is possible to collect the biometric data while the user simultaneously performs some other function(s) using the photodetector array, such as controlling functionalities of a second device.

Some conventional devices perform biometric detection by requiring a user to contact a photodetector or other type of detector in a prescribed manner. For example, a pulse oximeter may require a user to place a finger within a clip that contains a light source and light detector. In other examples, wearable devices such as fitness watches may contact a user while being worn.

In these and other scenarios, a PPG sensor, as referenced above, may measure various biometric parameters of the user. Such conventional systems may perform a thresholding function, e.g., to ensure that the user's finger is placed in an expected position within a pulse oximeter relative to the light source/light detection being used, or to ensure that a PPG sensor of a wearable device (e.g., a watch) is sufficiently stable relative to a wearing user to ensure a desired level of accuracy of PPG measurements.

Although these and similar techniques provide many advantages, such techniques also suffer from various shortcomings. For example, the user may be required to proactively and correctly position the user's finger within a pulse oximeter for a minimum quantity of time to obtain a desired measurement. Similarly, some wearable devices, such as wearable watches, provide intermittent heartrate detection by requiring a user to touch a sensor coupled to the watch when a heartrate measurement is desired. In these and other examples, conventional PPG sensors in wearable devices add costs to such devices, may not be convenient to use, and/or may not provide desired types of measurements or levels of accuracy with respect to captured biometric data.

For example, a PPG sensor used in a watch may detect volumetric changes in a user's blood flow within one or more arteries of the user that underly the watch, while the watch is being worn. Accordingly, it is possible to capture heart rate or other data, without requiring the wearer of the watch to take a further, specific action (such as touching a sensor on the watch with a finger surface).

However, in many cases, the user's artery may move relative to the PPG sensor as part of normal user motion. Such movement may reduce an accuracy of corresponding PPG measurements, particularly when the user is moving and/or when continuous measurements are desired.

To address such difficulties, many conventional PPG sensors use additional hardware (and associated software), such as accelerometers, and/or multiple light sources with multiple frequencies. For example, such devices may implement a multi-path approach that utilizes the different features of different wavelengths of light being used to account for, e.g., the type of arterial movements just referenced. For example, such PPG sensors may use infrared (IR), red, and green light sources.

Such approaches add cost to the wearable device. Moreover, different wavelengths of light have different levels of penetration with respect to the user's skin, with corresponding different levels of ability to detect and measure arterial changes in a desired manner. For example, IR light may be preferable from the perspective of achieving desired levels of skin penetration, but green light may be required to achieve the types of multipath solutions referenced above.

In techniques described herein, however, it is possible to use a photodetector array of individual photodetectors to collect biometric data from any of a number of different subsets of the photodetector array and during a plurality of touch events. Accordingly, biometric data may be collected across a large number of touch events of the user, and/or may account for movements of the user during measurements (including, e.g., finger or arterial movements).

As a result, for example, it is possible to make passive, continuous heart rate measurements, without requiring the use of a multipath solution, such as the multi-color approach referenced above. By using IR light with the described techniques, for example, greater depth of skin penetration may be obtained, costs may be reduced, and reliability and accuracy may be improved.

Moreover, desired measurements may be obtained without requiring proactive actions on the part of the user (such as requiring the user to touch a specified surface), in a specified manner, and for a specified time, with the intent of obtaining heart rate measurements. Instead, for example, biometric measurements may be obtained even when the user contacts a photodetector surface for some other purpose, and/or without any specific or separate request for biometric measurements to be taken.

Figure 3:
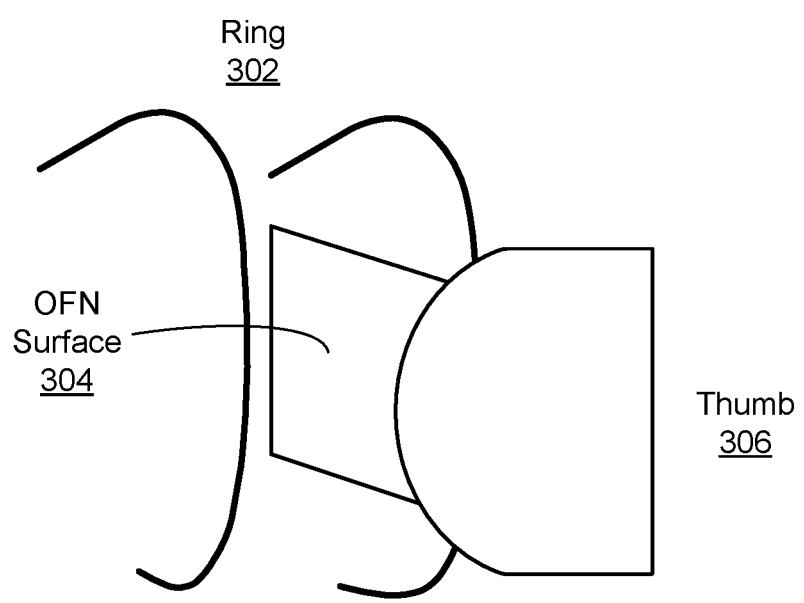
FIG. 3 illustrates an example implementation of the system of FIG. 1.
Figure 4:
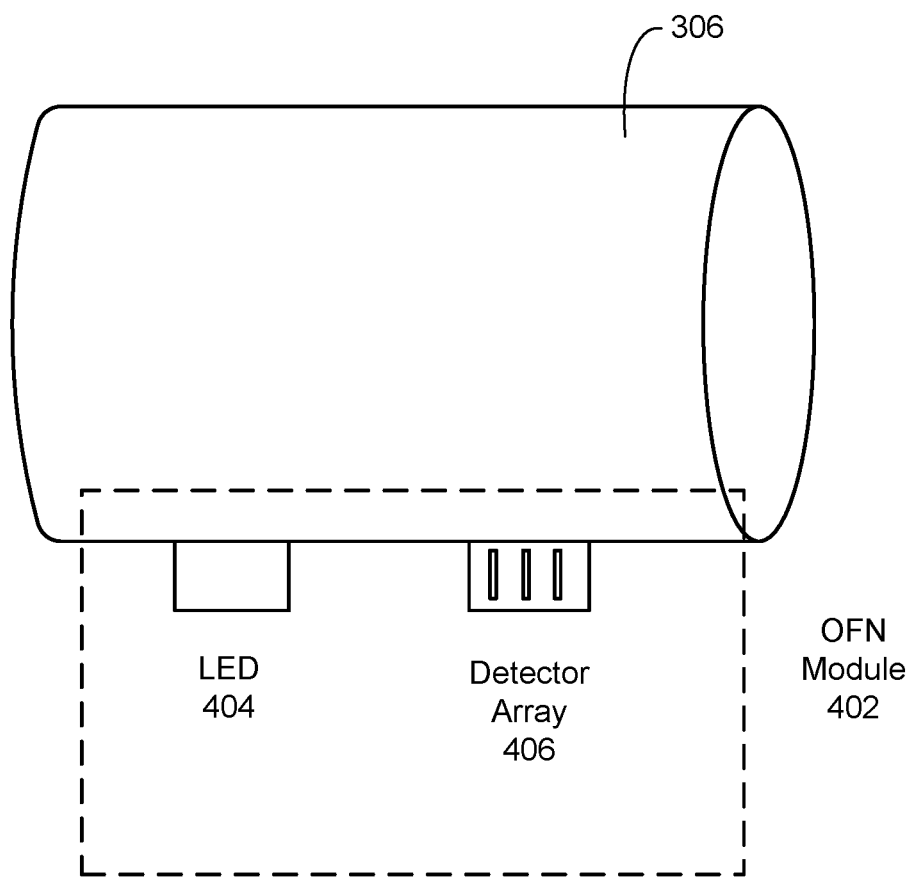
FIG. 4 illustrates additional details regarding the example implementation of FIG. 3.

For example, as shown in the examples of FIGS. 3 and 4, an optical finger navigation (OFN) surface of an OFN system may be configured to implement the techniques described herein for collecting biometric data. Then, when the OFN system is used for an intended purpose, such as controlling functionalities of devices such as augmented reality (AR) glasses, or other device(s), specified biometric data may passively and simultaneously be collected.

For example, a user may repeatedly or frequently use an OFN system to control AR glasses, or other devices. During such use, when the user contacts the OFN system in manners that are determined to be compatible with biometric detection as described herein, such biometric detection may be performed across a number of touch events performed by the user when controlling the AR glasses. By their nature, such touch events may be performed over the course of a period of time, such as hours, days, or weeks. Then, for example, user heart rate data may be captured, aggregated, and analyzed over the relevant period of time, to thereby discern trends or otherwise interpret the collected data. Resulting conclusions from such data analysis may be provided to the user, so that the user obtains desired information in a manner that is cost-effective, and that does not require separate, conscious action for the purpose of triggering heart rate measurements for obtaining the desired information.

FIG. 1 is a block diagram of a system for biometric detection using a photodetector array. In FIG. 1, an array-based biometric detector 102 is illustrated as being worn or held by a user 104, as part of a computing device 106.

In the example of FIG. 1, the computing device 106 may be worn at the end of an arm of the user 104, e.g., on the user's wrist, hand, or finger. Thus, the computing device 106 may be implemented using, e.g., a watch, a band, a strap, a bracelet, or a ring.

However, as referenced in more detail below, such examples are non-limiting, and the computing device 106 may be worn on any suitable or desired body part of the user 104 for purposes of capturing desired gestures. For example, the computing device 106 may be worn on a user's leg (e.g., ankle), or may be integrated into a head-mounted device (HMD), including smartglasses. In still other examples, the computing device 106 may be integrated into items of clothing, such as gloves, socks, belts, or shirt sleeves. Specific examples of wearable versions of the computing device 106 of FIG. 1 are provided below, with respect to FIGS. 11 and 12.

In additional or alternative examples, the computing device 106 may be held by the user 104. For example, FIG. 13, described below, illustrates an example of a held implementation of the computing device 106, using a smartphone. However, the computing device 106 may be configured as a held implementation in many different ways, and using many different form factors. For example, the computing device 106 may be constructed as part of a joystick or other gaming device for gaming implementations, or as part of any held I/O device for controlling a computer or other device.

In general, wearing the computing device 106 thus refers to any scenario in which the computing device 106 remains on a body part of the user 104, without requiring further action on the part of the user 104. Holding the computing device 106 refers to scenarios in which the computing device 106 is maintained in contact with, or in the physical possession of, the user 104, as a result of an action of the user 104 that is maintained during the holding. For example, such holding may include grasping, grabbing, or carrying.

It is possible to both wear and hold the computing device 106 at a same or overlapping time. For example, the computing device 106 may be worn on one arm or hand, and held by the other hand at the same time, or may be worn in a position in which it is possible to be held (e.g., at the end of a sleeve, or on another article of clothing).

FIG. 1 further illustrates that the computing device 106 may include a body 107. As may be appreciated from the various examples provided herein, the body 107 may be any housing or casing suitable for enabling the wearing or holding of a particular implementation of the computing device 106.

The body 107 may be configured for the mounting of, or coupling to, one or more sensors and other components, including a light source 108 and a photodetector array 110, e.g., a photodetector array. For example, the light source 108 may represent a light emitting diode (LED) providing one or more wavelengths of light. The photodetector array 110 may include a plurality of light-detecting surfaces (e.g., pixels, or groups of pixels) configured to capture light from the light source 108 that is transmitted through, or reflected from, the user 104.

In FIG. 1, the photodetector array 110 is also illustrated in an expanded view that demonstrates individual photodetectors of the photodetector array 110. For example, the individual photodetectors of the photodetector array may represent individual pixels, groups of pixels, or pixel regions.

In the simplified example of FIG. 1, the photodetector array 110 is illustrated as a 4×4 array. In various implementations, the photodetector array 110 may be implemented in any desired size or shape, such as the n×n example of FIG. 1, or n×m. The photodetector array 110 need not be periodic or symmetrical, and may include any plurality of photodetectors grouped for the purposes of using the techniques described herein.

The expanded view of the photodetector array 110 includes, among the 4×4 array, photodetectors 110a, 110b, 110c, and 110d. A touch surface 105 represents a detected point of contact between the user 104 and the photodetector array 110, which may occur during a touch event of the user 104 with the photodetector array 110.

For example, the touch surface 105 may represent a fingertip of the user 104 being pressed against a surface of the photodetector array 110. In more general examples, the touch surface 105 may represent any skin surface of the user 104 in contact with the photodetector array 110. An intervening surface (e.g., a screen protector) may be present between the skin surface of the user 104 and the photodetector array 110, for example, when the intervening surface permits sufficient levels of light transmission and reflection.

In a simplified example, the touch surface 105 may be constant for a period of time. As discussed below, in other examples, the touch surface 105 may move in conjunction with movements of the user 104.

As shown in FIG. 1, the touch surface 105 may only cover, touch, occlude, or otherwise be associated with some of (a subset of) the individual photodetectors of the photodetector array 110. In the example, the touch surface 105 at least partially covers individual photodetectors 110a, 110b, 110c, and 110d.

As may also be observed, an extent of coverage of the individual photodetectors 110a, 110b, 110c, and 110d varies across the touch surface 105. For example, only a small portion of the individual photodetector 110a is covered by the touch surface 105, while almost an entirety of the individual photodetector 110b is covered.

Consequently, some of the individual photodetectors 110a, 110b, 110c, and 110d may be ineligible for use or inclusion by the array-based biometric detector 102 when determining biometric data for the user 104. For example, signals detected by either of the individual photodetectors 110a, 110b may not provide any useful biometric data, due to the small degree of coverage by the touch surface 105.

Conversely, signals detected by either of the individual photodetectors 110c, 110d may possibly be used to determine biometric data, depending on various other factors. However, even with the illustrated extensive coverage of individual photodetectors 110b, 110d, detection signals from either or both of the individual photodetectors 110b, 110d may be discarded if the signal quality is low, or if the touch event is short or sporadic, or if the signals are otherwise determined to be unusable in providing reliable biometric data.

Put another way, the array-based biometric detector 102 may be configured to determine candidate photodetectors of the photodetector array 110 for potential use in determining biometric data for a touch event, and may be further configured to select a subset of the candidate photodetectors to generate the biometric data. The touch event may span a time interval, during which the touch surface 105 may move, re-locate, and/or remain stationary, in conjunction with corresponding movements of the user 104.

In some cases, for example, as referenced above, touch events and corresponding touch surfaces and movements may result in unusable or unreliable data. Nonetheless, over longer periods of time (and corresponding numbers of touch events), the array-based biometric detector 102 may collect sufficient quantities of data, in sufficient numbers and types of contexts, to generate significant and highly useful quantities of biometric data. Moreover, as the array-based biometric detector 102 is configured to determine whether and when to generate biometric data in conjunction with corresponding touch events, the user 104 is not required to take any specific action to generate the biometric data. Instead, the user 104 may use the photodetector array 110 for a separate purpose (such as, e.g., optical finger navigation, as described herein), and the array-based biometric detector 102 may passively collect desired biometric data in a highly reliable, convenient, accurate, and cost-effective manner.

To perform the above and related functionalities, the array-based biometric detector 102 includes a frame buffer 120, which is configured to collect and store sequences of image frames collected by the photodetector array 110. For example, the frame buffer 120 may continuously store image frames from the photodetector array 110, and may delete stored frames after a defined period of time, or after a maximum number of frame is reached, or after a specific quantity of memory is used, and/or based on other deletion criteria. In other examples, during a touch event that occurs over a time interval, the frame buffer 120 may collect and store image frames from the time interval.

A touch event analyzer 122 may be configured to analyze frames from the frame buffer 120. For example, the touch event analyzer 122 may be configured to analyze a set of frames to determine whether an occurrence of a touch event captured in the set of frames is of sufficient quality and extent to use in generating biometric data. For example, the touch event analyzer 122 may detect candidate photodetectors that have any degree of coverage by the touch surface 105, and may perform a thresholding or gating function to select a usable subset of the candidate photodetectors for biometric data generation.

For example, the touch event analyzer 122 may be configured to select a subset of photodetectors for each frame for which corresponding detection signals are of sufficient quality to use in generating biometric data, and further configured to determine whether the set of frames as a whole provides usable data for biometric data generation. In more specific examples, the touch event analyzer 122 may be configured to perform a spatiotemporal grouping of relevant pixel regions over time and across multiple frames of the frame buffer 120, including measuring a group set consistency, to confirm a that usable touch event has occurred (e.g., a usable user finger contact).

For example, the user 104 may touch the photodetector array 110 with varying degrees of firmness or smoothness. For example, the user 104 may move the user's finger (or other skin surface or point of contact) over the photodetector array 110 in a smooth, continuous manner (as opposed to a sporadic, intermittent, or irregular manner). The touch event analyzer 122 may perform the type of spatiotemporal grouping referenced above for detection signals associated with touch events, for a single frame and across a set of frames, to evaluate the touch event as a whole.

If validated by the touch event analyzer 122, collected data for a touch event, captured within a set of frames in the frame buffer 120, may be processed and provided to a biometric generator 124 to generate desired types of biometric data. For example, spectral analysis of the relevant set of frames may be performed for each frame (e.g., for each subset of selected photodetectors of each frame), so that measurements obtained from the series of frames provides a time series of data that represents biometric data of the user 104, such as a heartrate of the user 104.

As referenced above, such biometric data may be processed and used for many purposes. For example, over a period of time, the biometric data may be analyzed in the aggregate to discern trends or anomalous events. In other examples, as described below with respect to FIG. 10, the biometric data may be used to authenticate the user 104 with respect to using the computing device 106, or another device(s).

As also referenced above, the biometric data may be collected while the user 104 is using the computing device 106 to perform separate functions, such as optical finger navigation. The computing device 106 should thus be understood to include any computing device(s) that might benefit from, or be able to perform, the various functionalities just referenced.

Therefore, in the example of FIG. 1, the computing device 106 is broadly illustrated as including at least one processor 112, a non-transitory computer-readable storage medium 114, various types of input/output (I/O) hardware 116, and a function manager 118. The computing device 106 should be understood to potentially represent two or more computing devices in communication with one another, some examples of which are provided herein. The at least one processor 112 may thus represent one or more processors on such computing device(s), which may be configured, among other functions, to execute instructions stored using the non-transitory computer-readable storage medium 114.

As the at least one computing device 106 may represent many types of computing devices, examples of which are provided herein, the many types of input/output (I/O) hardware that may be used in such computing devices are illustrated in the aggregate in FIG. 1 as I/O hardware 116. By way of non-limiting example, such I/O hardware may include a display (e.g., a touchscreen), a button, a speaker or audio sensor, haptic sensor or output, camera, or a peripheral device (e.g., mouse, keyboard, or stylus).

In addition to the I/O hardware 116, the at least one computing device 106a may execute and provide many types of software that utilizes, or is implemented by, the at least one processor 112, the non-transitory computer-readable storage medium 114, and the I/O hardware 116. Such software (and associated functionality) is included and represented in FIG. 1 by a function manager 118.

That is, for purposes of the description of the simplified example of FIG. 1, the function manager 118 should be understood to represent and encompass the implementation of any software that may be associated with operation of the I/O hardware 116. For example, the function manager 118 may include an operating system and many different types of applications that may be provided by the at least one computing device 106a, some examples of which are provided in more detail, below.

For example, the function manager 118 may be used to provide optical finger navigation, using the light source 108, the photodetector array 110, and appropriate hardware of the I/O hardware 116. The function manager 118 also may be configured to provide the various types of biometric data analysis described herein. The function manager 118 also may be configured to provide any supplemental functionalities, such as authentication, that may benefit from or utilize the collected biometric data.

In order to facilitate operation of the array-based biometric detector 102 with the function manager 118, a function interface 126 may be configured to communicate with the function manager 118 to implement corresponding functions. As just referenced, the corresponding function may be related to any desired use or processing of collected biometric data by the function manager 118.

In some implementations, feedback may be provided to the user 104, characterizing the biometric data. For example, the function interface 126 may instruct the function manager 118 to provide visual, audio, or haptic indicators to the user 104 when the biometric data being collected indicates a negative event (e.g., excessively high heartrate).

Figure 2:
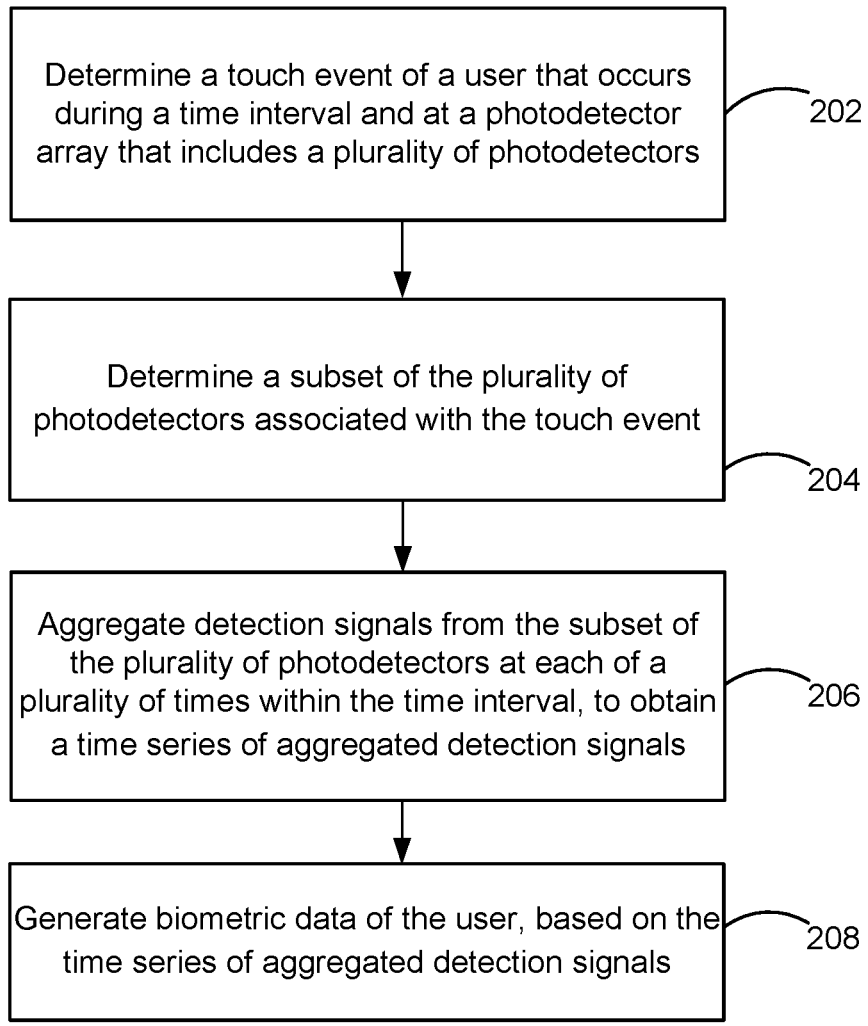
FIG. 2 is a flowchart illustrating example operations of the system of FIG. 1.

FIG. 2 is a flowchart illustrating example operations of the system of FIG. 1. In the example of FIG. 2, operations 202-208 are illustrated as separate, sequential operations. However, in various example implementations, the operations 202-208 may be implemented in an overlapping or parallel manner, and/or in a nested, iterative, looped, or branched fashion. Further, various operations or sub-operations may be included, omitted, or substituted.

In FIG. 2, a touch event of a user may be determined that occurs during a time interval and at a photodetector array that includes a plurality of photodetectors (202). For example, frames from the frame buffer 120, collected from the photodetector array 110, may be analyzed by the touch event analyzer 122 to determine whether a touch event has occurred.

A subset of the plurality of photodetectors associated with the touch event may be determined (204). For example, the touch event analyzer 122 may be configured to determine candidate photodetectors associated with each frame which may have sufficient signal strength and other characteristics for biometric data generation. The touch event analyzer 122 may test the signals from the candidate photodetectors to select the subset of the plurality of photodetectors to be used in biometric data generation. The subset of the plurality of photodetectors may be evaluated individually and as a whole, and from frame to frame. Thus, frames may also be evaluated individually and together. For example, a group set consistency of the subset of photodetectors may be evaluated across multiple frames. Examples of touch event detection and analysis are provided in detail below, e.g., with respect to FIG. 8.

Detection signals from the subset of the plurality of photodetectors at each of a plurality of times within the time interval may be aggregated, to obtain a time series of aggregated detection signals (206). For example, the biometric generator 124 may perform spatial averaging and pooling of signal strengths of each frame, so that the plurality of spatially averaged, pooled frames effectively form a time series.

Biometric data of the user may be generated, based on the time series of aggregated detection signals (208). For example, the biometric generator 124 may perform a spectral analysis and filtering of the time series to obtain a heart rate measurement.

FIGS. 3-6C illustrate an example use case scenario in which an optical finger navigation (OFN) module on a ring allows users to navigate and interact with smartglasses (e.g., AR glasses), or other devices. The array-based biometric detector 102 of FIG. 1 may be configured to use such an OFN module on an AR ring to opportunistically monitor user biometrics, such as measuring heart rate and heart rate variability, during the few seconds the user 104 interacts with the AR glasses, and without an explicit user trigger. As referenced above, the array-based biometric detector 102 may be used to measure small blood vessel volume changes from a series of color-amplified OFN images. The array-based biometric detector provides an example of a passive health monitoring system, with no cognitive load required from the user 104 to initiate a measurement.

Thus, even though described implementations may not be equipped with a dedicated PPG sensor, the described implementations may nevertheless decode optical imaging results from the OFN system, and solve a blind source separation problem to accurately recover human pulse and other biometrics. As a result, for example, cardiovascular information may be stored daily, and a screener may be built to alert users of abnormal conditions (e.g. bradycardia, tachycardia) for early detection, even when the user 104 is simply conducting normal daily activities.

FIG. 3 illustrates the example implementation of the system of FIG. 1 just referenced above. In FIG. 3, the computing device 106 is implemented as a ring 302 having an optical finger navigation (OFN) surface 304. As referenced above, the OFN surface 304 may utilize the photodetector array 110 and associated hardware/software (not shown separately in FIG. 3) to enable a thumb 306 of the user 104 to provide input and otherwise control functions of the ring 302, or of another device. For example, the user 104 may be wearing smartglasses, and may use the OFN surface 304 to control functions of the smartglasses, such as screen navigation of a screen of the smartglasses.

Whenever the user 104 uses the OFN surface 304, the array-based biometric detector 102 may determine whether the current use of the OFN surface 304 constitutes a touch event that may be used for biometric data generation. For example, a surface of the thumb 306 may provide a touch surface corresponding to the touch surface 105 of FIG. 1.

For example, the ring 302 may be worn on an index finger of the user 104. The base of the thumb 306 may touch the part of the ring 302 where the OFN surface 304 is visible.

FIG. 4 illustrates additional details regarding the example implementation of FIG. 3. Specifically, FIG. 4 illustrates that an OFN module 402 may be used to provide the OFN surface 304 of FIG. 3, and may include an LED 404 and a photodetector array 406, corresponding to the photodetector array 110 of FIG. 1. As described above, light from the LED 404 may be reflected from the thumb 306 and the reflected light may be detected by the photodetector array 406.

Figure 5:
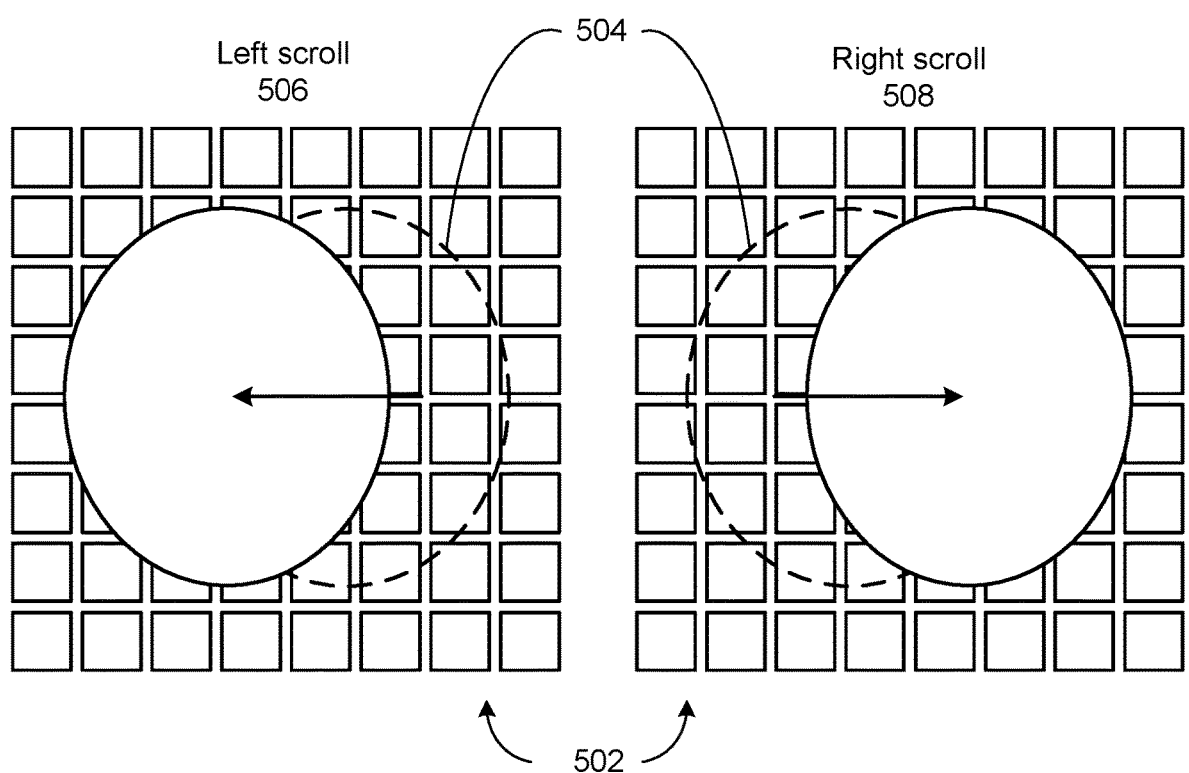
FIG. 5 illustrates example movement detection techniques that may be used in the example implementation of FIG. 3.

FIG. 5 illustrates a photodetector array 502 providing a more detailed example of the photodetector array 406. A touch surface 504 may be detected by the OFN module 402. A left scroll 506 may be detected when the user moves the user's thumb 306 to the left, and a right scroll 508 may be detected when the user moves the user's thumb 306 to the right.

Thus, using a mini LED source (e.g., the LED 404) that shines infrared light towards thumb 306, and the photodetector array 406 that receives reflected optical energy, reflected optical energy may be measured and used to control the ring 302, AR glasses, or other device(s).

Once the thumb-to-OFN contact is established, a pixel in the OFN surface 304 (illustrated as a 8×8 optical photodetector array 502 in FIG. 5) can sense whether a region of the finger is touching the photodetector array 502 by measuring the optical reflection energy. By aggregating the total response over multiple pixels and computing optical flow, the OFN module 304 can determine the subtle direction of thumb movement. As referenced, this direction estimate may be provided to an AR glasses interface to control a menu screen or other operation of the AR glasses.

The user 104 may perform the scroll operations 506, 508 and many other types of navigations or uses of the OFN module 402, at many different times of the day. The user 104 is not required to request detection or collection of biometric data in conjunction with such OFN use. Nonetheless, the array-based biometric detector 102 may be configured to determine whether it is feasible to generate and collect biometric data at each potential touch event associated with use of the ring 302 of FIG. 3.

Figure 6A:
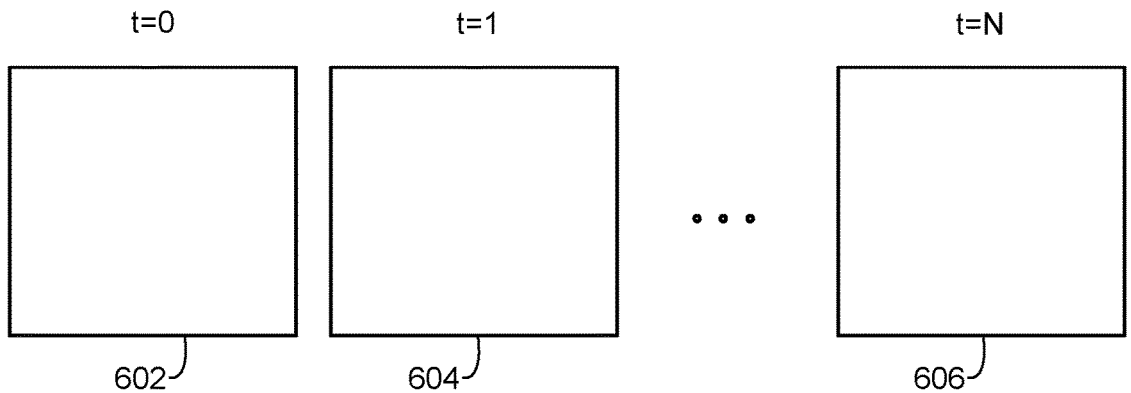
FIGS. 6A, 6B, and 6C illustrate example use case scenarios for the example of FIG. 5.
Figure 6B:
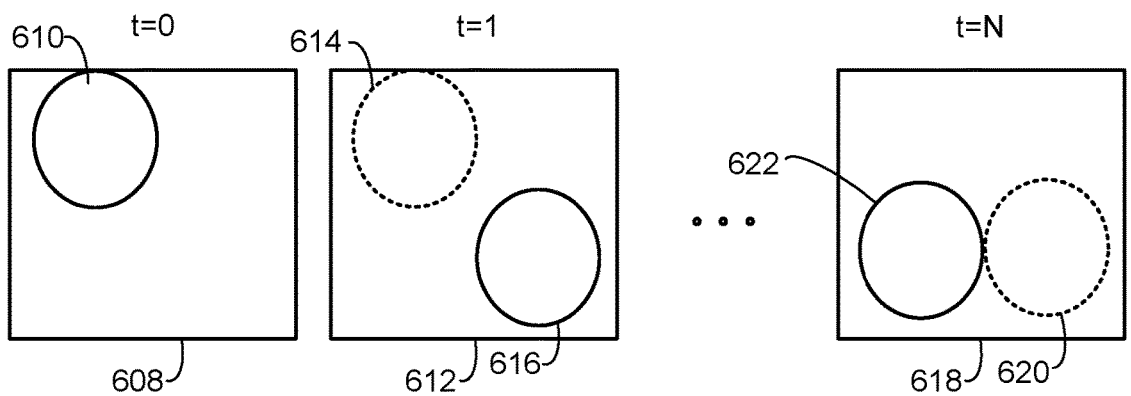
Figure 6C:
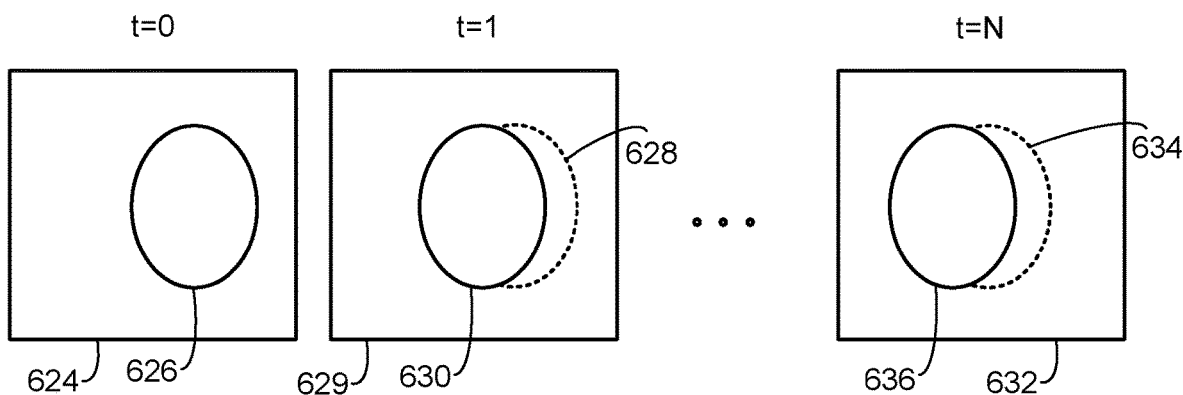

For example, FIGS. 6A-6C provide example image frames illustrating touch events and associated contexts for the spatiotemporal grouping strategies described herein. Such strategies may be used to determine whether a given time period is a good time to measure heart rate or otherwise generate biometric data.

For example, in FIG. 6A, frame 602, frame 604, and frame 606 represent a series of frames captured and stored within the frame buffer 120 of FIG. 1, at times t=0, t=1, and t=N, respectively. In the example of FIG. 6A, no touch event is detected.

In FIG. 6B, a frame 608 at time t=0 is illustrated as having captured a touch surface 610. A subsequent frame 612 at time t=1 illustrates a touch surface 616, separately located from the previous touch surface 610 (represented for comparison in frame 612 by dotted lines 614). Similarly, a subsequent frame 618 at time t=N illustrates a touch surface 622, separately located from the previous touch surface 616 (represented for comparison in frame 618 by dotted lines 620).

Thus FIG. 6B illustrates a case in which a touch event is made, but includes relatively high velocity and sporadic touch surface contacts and movements. For example, FIG. 6B may represent use of the OFN module 402 to perform click events, or may represent non-thumb artifacts such as incidental touches of the OFN surface 304. FIG. 6B therefore illustrates a scenario in which it is unlikely that a reliable heart rate measurement could or should be made, and may therefore be rejected as a potential touch event for biometric data generation. For example, the touch event analyzer 122 may reject the example of FIG. 6B, using the techniques describe in detail below with respect to FIG. 8.

In FIG. 6C, a frame 624 at time t=0 is illustrated as having captured a touch surface 626. A subsequent frame 629 at time t=1 illustrates a touch surface 630, separately located from the previous touch surface 626 (represented for comparison in frame 629 by dotted lines 628). Similarly, a subsequent frame 632 at time t=N illustrates a touch surface 636, separately located from the previous touch surface 630 (represented for comparison in frame 632 by dotted lines 634).

Thus FIG. 6C illustrates a case in which a touch event is made, and the touch event is spatially and temporally coherent and smooth. For example, FIG. 6C may represent or correspond to the example scrolling operations of FIG. 5. FIG. 6C therefore illustrates a scenario in which it is likely that a reliable heart rate measurement may be made, and may therefore be accepted as a potential touch event for biometric data generation. For example, the touch event analyzer 122 may accept the example of FIG. 6C, using the techniques describe in detail below with respect to FIG. 8.

Figure 7A:
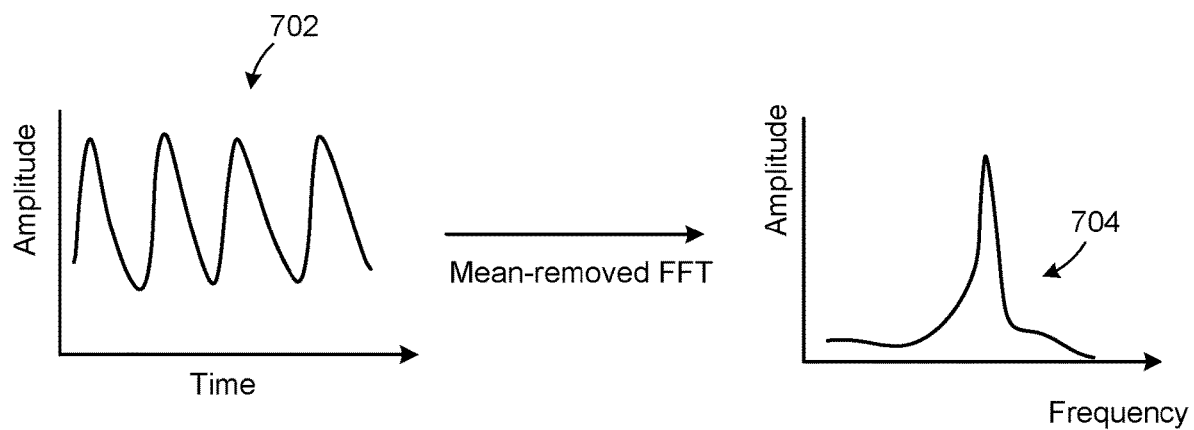
FIGS. 7A and 7B illustrate example heart rate detection techniques implemented using the system of FIG. 1.
Figure 7B:
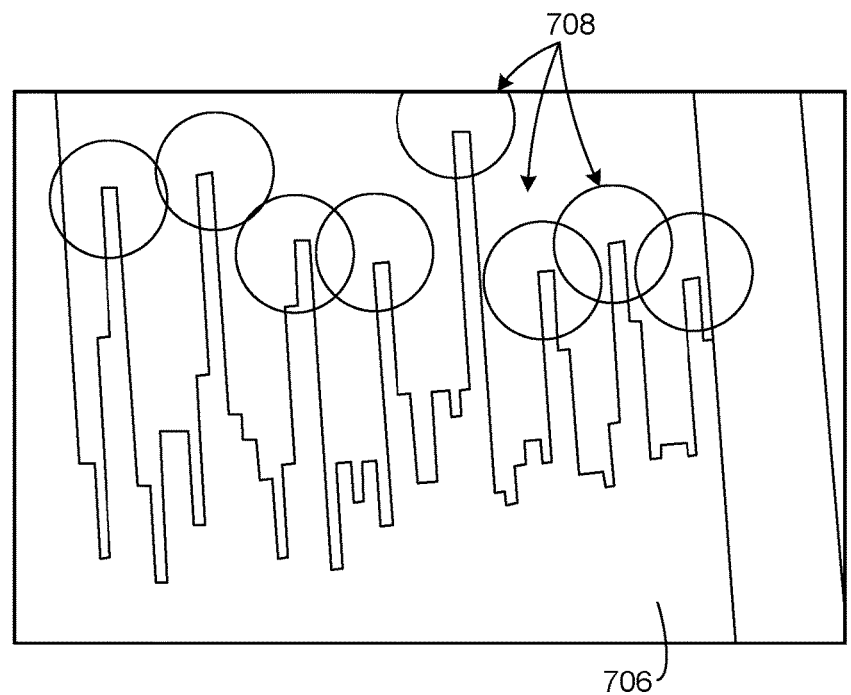

FIGS. 7A and 7B illustrate example heart rate detection techniques implemented using the system of FIG. 1. FIGS. 7A and 7B illustrate that the system of FIG. 1 may be used to mimic or otherwise provide a proxy or de facto PPG signal, without requiring use of a dedicated PPG sensor.

As referenced above with respect to such PPG sensors, for every beat of pulse of the user 104, the user's heart pumps blood throughout the user's body. With respect to the thumb 306 of FIG. 3, there is thus a small change in volume in blood vessels under the thumb 306. In general, light absorption from the light of the LED 404 of FIG. 4 may depend on various factors related to, e.g., the user 104 and the light being used.

For example, a reflected signal may be characterized by degrees of absorption due to skin, bone, and tissue, and absorption due to venous blood. Absorption due to non-pulsatile arterial blood effectively provides a DC component to the reflected signal, while absorption due to pulsatile arterial blood provides an AC signal. The AC signal, although considerably smaller in magnitude than the DC component, has an oscillation rate that correspond to the heart rate of the user 104. A resulting signal would be similar to the example of FIG. 7A, which illustrates a time-varying signal 702.

Using the techniques of FIG. 1 and otherwise as described herein, the signal 702 may be created using a plurality of frames of the frame buffer 120. Then, as also illustrated in FIG. 7A, a mean-subtracted fast Fourier transform (FFT) of the waveform 702 may be computed in order to represent the waveform 702 using a phase-invariant feature. An example process may include first removing a mean component of the waveform 702 (e.g., stemming from the various absorption parameters and associated DC components referenced above), because the corresponding signal amplitude offset does not describe information related to a heartrate of the user 104. Then, a FFT signal 704 may be calculated from the resulting zero-mean signal to obtain a spectral feature.

By obtaining such high-amplitude frequencies, and because the human heart beats for a periodic set of events, a resulting frequency signal 706 may be obtained, as shown in FIG. 7B, in which the frequency signal 706 demonstrates peaks 708 in the spectrum representation. As referenced below, max-filtering techniques may then be used to select the peaks, which may then be saved as an estimate of a human heart rate of the user 104.

The above examples illustrate that pulse rate detection and other biometric data collection may be performed in an opportunistic, all-day fashion, including an ability to determine whether to initiate the relevant (e.g., heart rate) measurement algorithm at any given point in time. In the examples, this determination may be made using the described techniques for, for example, spatiotemporally grouping relevant pixel regions over time, and measuring the group set consistency to confirm a user finger contact. Then, once confidence is achieved that a specified, qualifying touch event has occurred, the types of spectral analysis referenced above may be used to compute an accurate pulse rate number.

Figure 8:
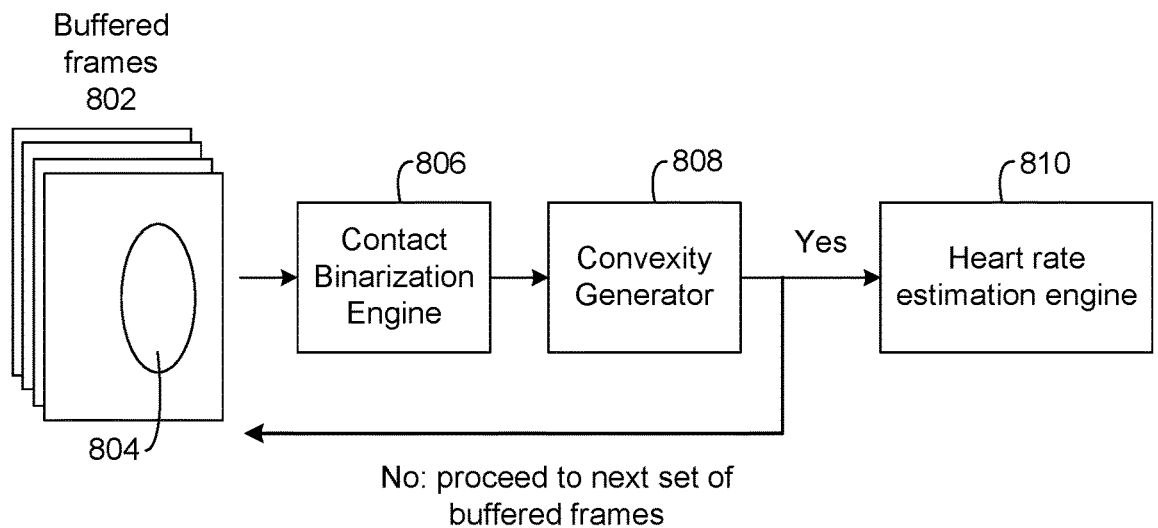
FIG. 8 is a block diagram illustrating an example implementation for touch event analysis in the system of FIG. 1.

FIG. 8 is a block diagram illustrating an example implementation for touch event analysis in the system of FIG. 1. That is, FIG. 8 provides specific example techniques for determining whether to initiate pulse rate estimation or other biometric data generation and collection.

In FIG. 8, a set of buffered frames 802 may be obtained from the frame buffer 120 of FIG. 1. As described with respect to FIGS. 1, 5, and 6A-6C, each frame may include detection signals corresponding to a touch surface 804.

Further in FIG. 8, the set of buffered frames 802 (e.g., stream of images) may be provided to a contact binarization engine 806. The contact binarization engine 806 may be configured to convert each continuous OFN image of the set of buffered frames 802 into a 0-1 image. The resulting binary image may be compressed for ease of parsing. For example, the contact binarization engine 806 may generate a binary image using a threshold that is calibrated based on an extent to which an average thumb reflects light back to the OFN module 402.

Then, the resulting stream of binary images enter a convexity generator 808 that generates a three-dimensional characterization of a convexity of the touch surfaces of the binary images. For example, a convex hull of each touch surface in each binary image may refer to the smallest convex set of the shape of each touch surface. For example, if the touch surface is considered a bounded subset, the convex hull may be represented as a shape enclosed around the subset.

In the context of FIG. 8, the convexity generator 808 thus effectively characterizes a spatiotemporal smoothness of the touch surfaces, within and among the binary images, to determine whether the touch surfaces represent a touch event suitable for biometric data generation, such as the type of touch event described and illustrated above with respect to FIG. 6C.

For example, such a convexity characterization may be determined using the equation: convexity_score=1/((convex hull of 3d binarization data)−(3d binarization data)). In the example, for 3D binarization data that is fully convex, the convexity_score would be a high number. Therefore, a convexity threshold may be set for the convexity_score, above which the input stream of images may be verified as being spatiotemporally coherent. If this threshold is met (yes), the set of buffered frames 802 may be provided to a heart rate estimation engine 810, representing an example implementation of the biometric generator 124. Otherwise (no), the process of FIG. 8 may be repeated for the next batch of buffered frames.

Figure 9:
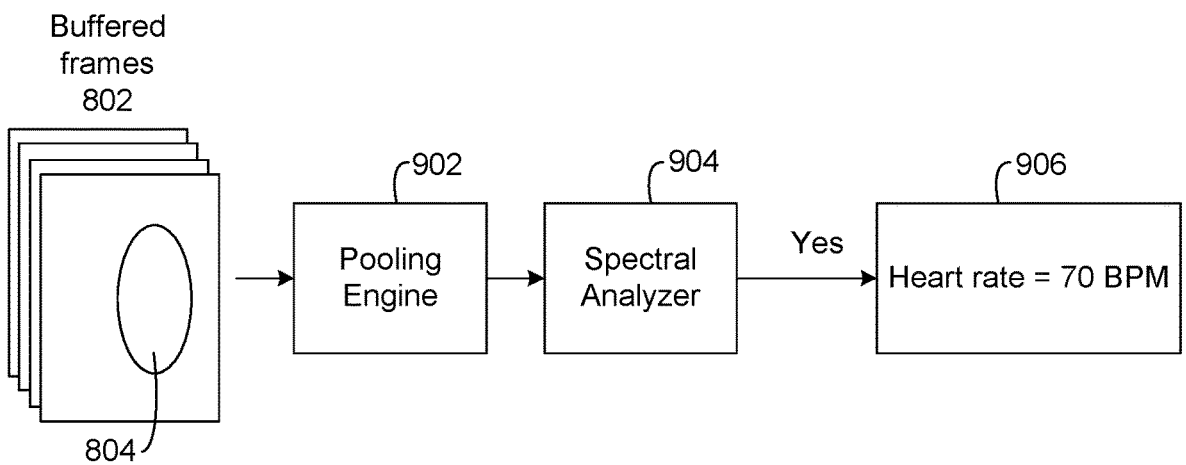
FIG. 9 is a block diagram illustrating an example implementation for heart rate estimation in the system of FIG. 1, and for the example of FIG. 8.

FIG. 9 is a block diagram illustrating an example implementation for heart rate estimation in the system of FIG. 1, and for the example of FIG. 8. That is, FIG. 9 represents an example implementation of the heart rate estimation engine 810 of FIG. 8, which may be used once sufficient confidence from spatiotemporal coherence checks exploiting spatial resolution of the OFN module 402 have been obtained to ensure that heart rate can be accurately measured.

In FIG. 9, the set of buffered frames 802 is illustrated as being input to a pooling engine 902. The pooling engine 902 provides a spatial mean pooling of each image of the set of buffered frames 802. That is, from the binarization operations of FIG. 8, a region of interest is defined for each image, and the OFN values within that image region may be averaged. In this way, each image may be summarized with a single number.

The resulting set of numbers for the set of buffered frames, being obtained over a time interval, provides a time series of numbers, and thereby provides a signal similar to a PPG signal, as described above with respect to FIGS. 7A and 7B. This time series may be provided to a spectral analyzer 904, which may be configured to remove the temporal mean of the time series signal and apply a FFT, as shown in FIG. 7A, to represent the high-amplitude frequencies in the signal. As already illustrated in FIG. 7B, because the human heart beats for a periodic set of events, the result would be a peaky frequency signal in the spectrum representation. Max-filtering may then be used to extract the value(s) of the frequency signal, which then corresponding to a determined estimate 906 of a heart rate of the user 104.

Figure 10:
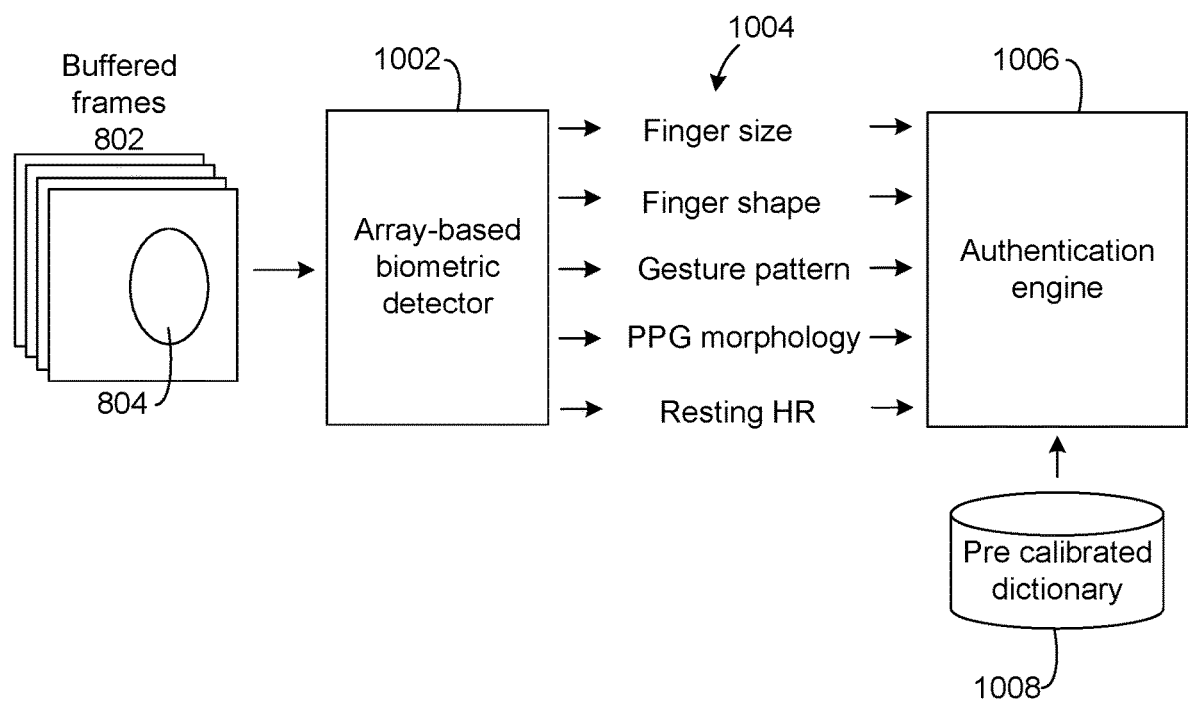
FIG. 10 is a block diagram of an example implementation of the system of FIG. 1 for authentication.

FIG. 10 is a block diagram of an example implementation of the system of FIG. 1 for authentication. FIG. 10 illustrates that an array-based biometric detector 1002 may be configured to utilize the set of buffered frames 802 to generate a set of biometric data 1004 to be used by an authentication engine 1006 to authenticate the user 104 with respect to using the computing device 106 of FIG. 1, or a connected computing device. For example, the authentication engine 1006 may be configured to compare the set of biometric data 1004 against a pre-calibrated dictionary 1008 of saved biometric data for the user 104, in order to authenticate the user 104.

For example, during a setup or initial use of the computing device 106, the user 104 may be requested and guided to participate in a calibration session designed to record specific gestures, navigation routines, or other uses of the photodetector array 110, such as tasks performed when using the OFN surface 304 of an OFN module 402. The calibration session may be designed to record any of the examples of the set of biometric data 1004, including a finger size, finger shape, gesture pattern of a specific gesture, a morphology of the proxy PPG signal described above with respect to FIGS. 7A, 7B, and 9, and a resting heart rate of the user 104.

During subsequent usage, the user may interact naturally with the computing device 106 (e.g., the ring 302 of FIG. 3). The relevant identification parameters may be provided by the array-based biometric detector 1002, and matched against the pre-calibrated dictionary 1008 by the authentication engine 1006.

Example matching processes may be performed using any suitable techniques. For example, classifiers, such as decision trees, may be used. The matching may assign different weights to the individual ones of the set of biometric data 1004. The matching may select individual ones of the set of biometric data 1004 for use in a particular authentication process, such as by selecting a minimum set of parameters which have the highest quality of measurement in a current interaction with the user 104.

Figure 11:
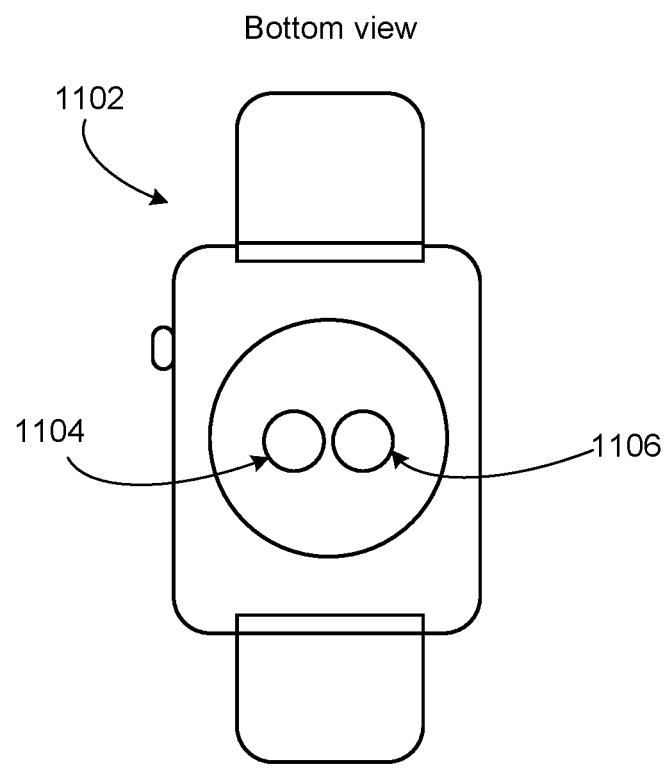
FIG. 11 is an example illustration of the system of FIG. 1, implemented using a smartwatch.

Advantageously, the user 104 need not be required to initiate an authentication process. Instead, the user 104 may simply use the computing device 106, e.g., the ring 302, in a standard manner, and authentication may run in the background FIG. 11 is an example illustration of the system of FIG. 1, implemented using a smartwatch 1102. More specifically, FIG. 11 illustrates a bottom view of the smartwatch 1102, illustrating a light source 1104 and a photodetector array 1106. During wear by the user 104, the light source 1104 and the photodetector array 1106 may thus be positioned appropriately with respect to a wrist of the user 104 to generate biometric data as described herein.

For example, during normal wear of the smartwatch 1102, the user 104 may perform normal daily movements. Moreover, the smartwatch 1102 may be fastened by the user 104 with various and varying levels of tightness. Consequently, a touch surface defined between the user 104 (e.g., at the user's wrist) and the smartwatch 1102 may also vary. Put another way, the smartwatch 1102 may move relative to the user 104 during normal wear.

Using the techniques described herein, however, the changing/moving touch surfaces may be tracked and analyzed to provide reliable biometric data. For example, touch surfaces may be tracked using the optical flow techniques described above in the context of optical finger navigation. In conventional smartwatches, for example, without such surface tracking and related concepts as described herein, motion artifacts may be present and may confound collection of desired data (e.g., heart rate measurements), even when multiple wavelengths of light are used. In FIG. 11, however, and as also referenced above, it is possible to collect such biometric data using a single wavelength of light, e.g., IR light. The user 104 may thus enjoy passive biometric data detection, collected reliably and accurately, in a low-cost manner.

Figure 12:
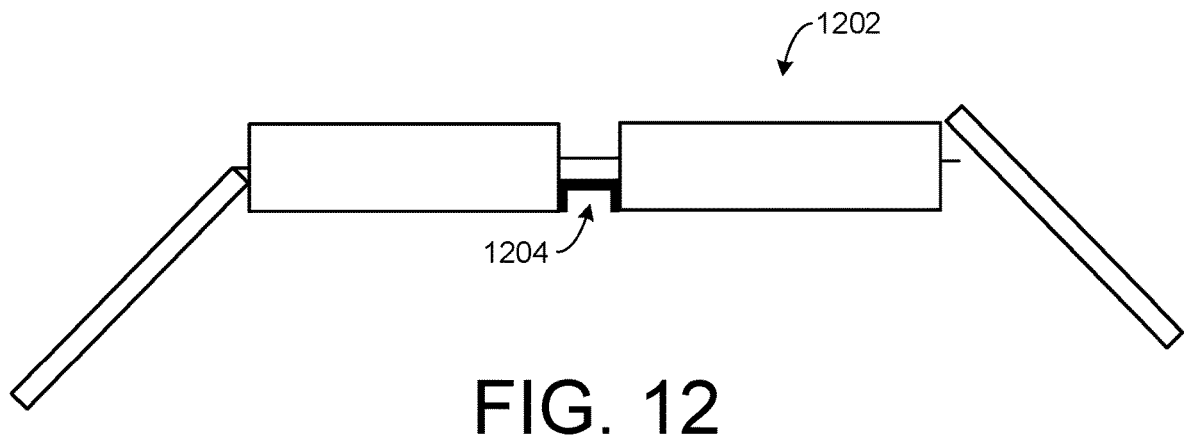
FIG. 12 is an example illustration of the system of FIG. 1, implemented using smartglasses.

FIG. 12 is an example illustration of the system of FIG. 1, implemented using smartglasses 1202. As shown, the smartglasses 1202 may include a nose bridge module 1204 that includes a light source and a photodetector array. The nose bridge module 1204, as with the smartwatch 1102 just described, may move relative to the nose of the user 104, but may still function to capture biometric data using the techniques described herein. Moreover, although illustrated with a nose bridge mounting, similar techniques may be implemented at other locations on the smartglasses 1202, such as on one or both arms thereof. In both the smartwatch 1102 and the smartglasses 1202, an OFN module may also be implemented.

Figure 13:
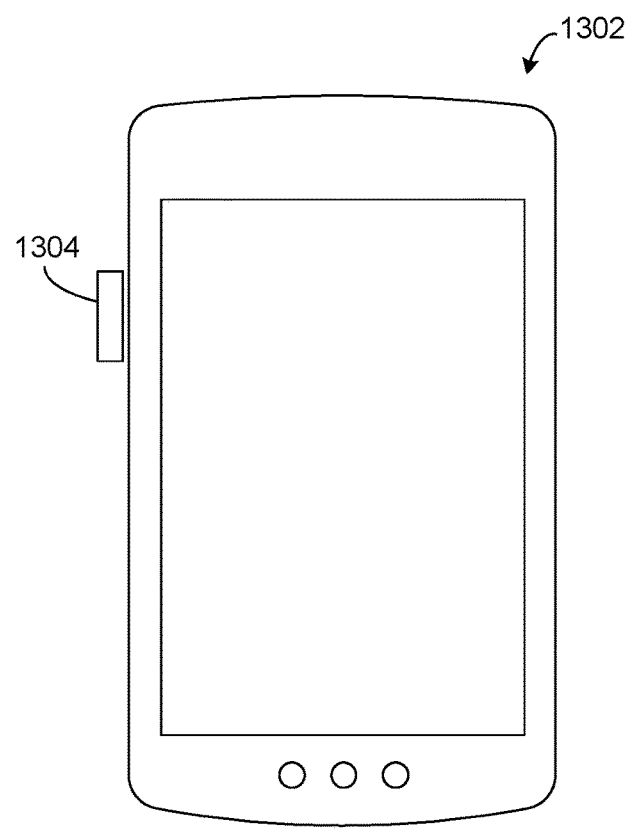
FIG. 13 is an example illustration of the system of FIG. 1, implemented using a smartphone.

FIG. 13 is an example illustration of the system of FIG. 1, implemented using a smartphone 1302. As shown, the smartphone 1302 may include an OFN module 1304, implemented using the techniques described herein.

Although shown mounted at a side of the smartphone 1302, the OFN module 1304 may be mounted at any desired location on the smartphone 1302. For example, the OFN module 1304 may be mounted on a back surface of the smartphone 1302, opposite a screen of the smartphone 1302. Then, the user 104 may perform navigation function with the OFN module 1304, while simultaneously viewing the screen of the smartphone 1302, and while biometric data is being passively collected.

Figure 14:
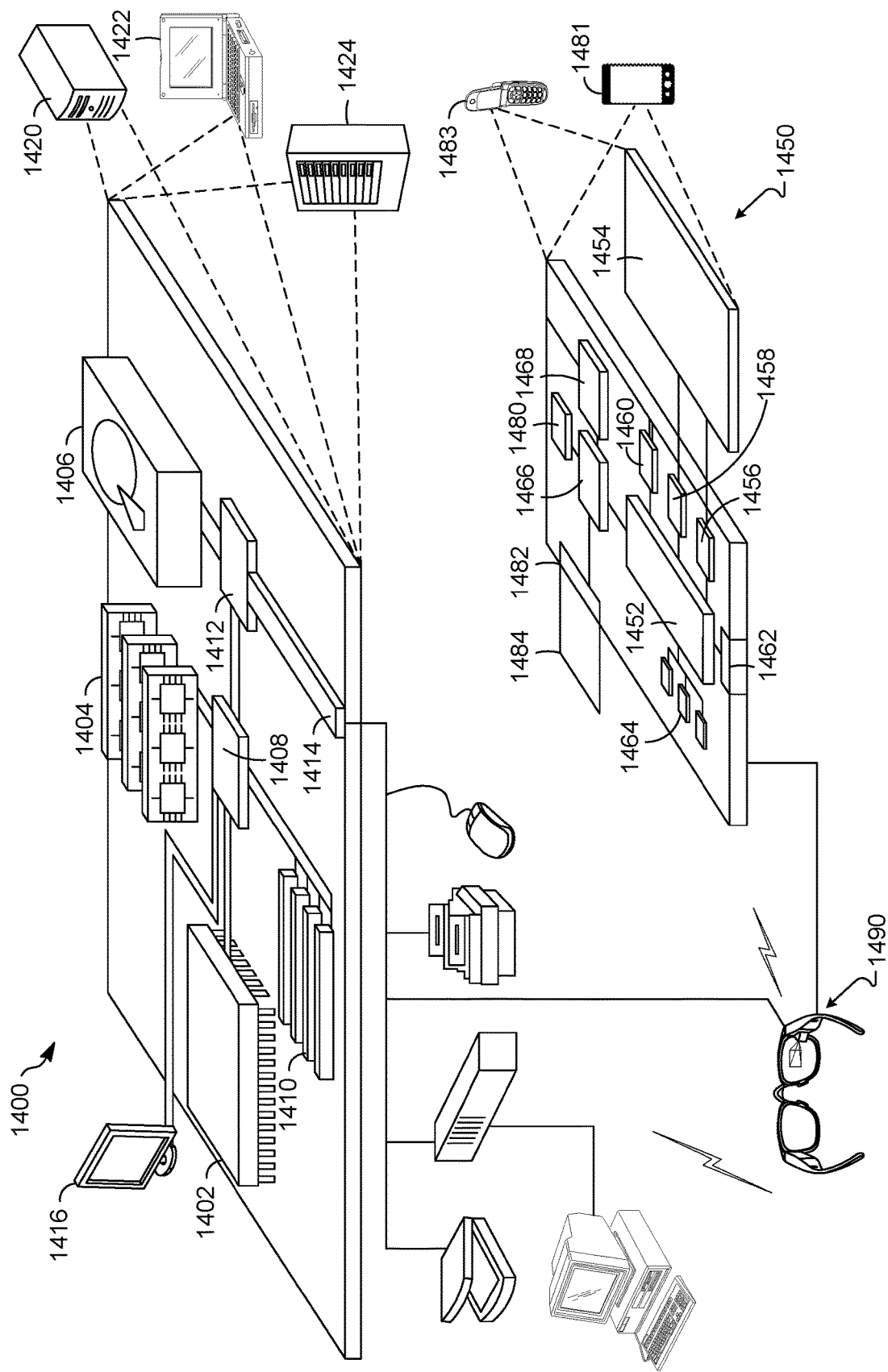
FIG. 14 shows an example of a computer device, mobile computer device and head mounted device according to at least one example implementation.

FIG. 14 shows an example of a computer device 1400 and a mobile computer device 1450, which may be used with the techniques described here. Computing device 1400 is intended to represent various forms of digital computers, such as laptops, desktops, tablets, workstations, personal digital assistants, smart devices, appliances, electronic sensor-based devices, televisions, servers, blade servers, mainframes, and other appropriate computing devices. Computing device 1450 is intended to represent various forms of mobile devices, such as personal digital assistants, cellular telephones, smart phones, and other similar computing devices. The components shown here, their connections and relationships, and their functions, are meant to be exemplary only, and are not meant to limit implementations described and/or claimed in this document.

Computing device 1400 includes a processor 1402, memory 1404, a storage device 1406, a high-speed interface 1408 connecting to memory 1404 and high-speed expansion ports 1410, and a low speed interface 1412 connecting to low speed bus 1414 and storage device 1406. The processor 1402 can be a semiconductor-based processor. The memory 1404 can be a semiconductor-based memory. Each of the components 1402, 1404, 1406, 1408, 1410, and 1412, are interconnected using various busses, and may be mounted on a common motherboard or in other manners as appropriate. The processor 1402 can process instructions for execution within the computing device 1400, including instructions stored in the memory 1404 or on the storage device 1406 to display graphical information for a GUI on an external input/output device, such as display 1416 coupled to high speed interface 1408. In other implementations, multiple processors and/or multiple buses may be used, as appropriate, along with multiple memories and types of memory. Also, multiple computing devices 1400 may be connected, with each device providing portions of the necessary operations (e.g., as a server bank, a group of blade servers, or a multi-processor system).

The memory 1404 stores information within the computing device 1400. In one implementation, the memory 1404 is a volatile memory unit or units. In another implementation, the memory 1404 is a non-volatile memory unit or units. The memory 1404 may also be another form of computer-readable medium, such as a magnetic or optical disk. In general, the computer-readable medium may be a non-transitory computer-readable medium.

The storage device 1406 is capable of providing mass storage for the computing device 1400. In one implementation, the storage device 1406 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods and/or computer-implemented methods, such as those described above. The information carrier is a computer- or machine-readable medium, such as the memory 1404, the storage device 1406, or memory on processor 1402.

The high speed controller 1408 manages bandwidth-intensive operations for the computing device 1400, while the low speed controller 1412 manages lower bandwidth-intensive operations. Such allocation of functions is exemplary only. In one implementation, the high-speed controller 1408 is coupled to memory 1404, display 1416 (e.g., through a graphics processor or accelerator), and to high-speed expansion ports 1410, which may accept various expansion cards (not shown). In the implementation, low-speed controller 1412 is coupled to storage device 1406 and low-speed expansion port 1414. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 1400 may be implemented in a number of different forms, as shown in the figure. For example, it may be implemented as a standard server 1420, or multiple times in a group of such servers. It may also be implemented as part of a rack server system 1424. In addition, it may be implemented in a computer such as a laptop computer 1422. Alternatively, components from computing device 1400 may be combined with other components in a mobile device (not shown), such as device 1450. Each of such devices may contain one or more of computing device 1400, 1450, and an entire system may be made up of multiple computing devices 1400, 1450 communicating with each other.

Computing device 1450 includes a processor 1452, memory 1464, an input/output device such as a display 1454, a communication interface 1466, and a transceiver 1468, among other components. The device 1450 may also be provided with a storage device, such as a microdrive or other device, to provide additional storage. Each of the components 1450, 1452, 1464, 1454, 1466, and 1468, are interconnected using various buses, and several of the components may be mounted on a common motherboard or in other manners as appropriate.

The processor 1452 can execute instructions within the computing device 1450, including instructions stored in the memory 1464. The processor may be implemented as a chipset of chips that include separate and multiple analog and digital processors. The processor may provide, for example, for coordination of the other components of the device 1450, such as control of user interfaces, applications run by device 1450, and wireless communication by device 1450.

Processor 1452 may communicate with a user through control interface 1458 and display interface 1456 coupled to a display 1454. The display 1454 may be, for example, a TFT LCD (Thin-Film-Transistor Liquid Crystal Display) or an OLED (Organic Light Emitting Diode) display, or other appropriate display technology. The display interface 1456 may comprise appropriate circuitry for driving the display 1454 to present graphical and other information to a user. The control interface 1458 may receive commands from a user and convert them for submission to the processor 1452. In addition, an external interface 1462 may be provided in communication with processor 1452, so as to enable near area communication of device 1450 with other devices. External interface 1462 may provide, for example, for wired communication in some implementations, or for wireless communication in other implementations, and multiple interfaces may also be used.

The memory 1464 stores information within the computing device 1450. The memory 1464 can be implemented as one or more of a computer-readable medium or media, a volatile memory unit or units, or a non-volatile memory unit or units. Expansion memory 1484 may also be provided and connected to device 1450 through expansion interface 1482, which may include, for example, a SIMM (Single In Line Memory Module) card interface. Such expansion memory 1484 may provide extra storage space for device 1450, or may also store applications or other information for device 1450. Specifically, expansion memory 1484 may include instructions to carry out or supplement the processes described above, and may include secure information also. Thus, for example, expansion memory 1484 may be provided as a security module for device 1450, and may be programmed with instructions that permit secure use of device 1450. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 1464, expansion memory 1484, or memory on processor 1452, that may be received, for example, over transceiver 1468 or external interface 1462.

Device 1450 may communicate wirelessly through communication interface 1466, which may include digital signal processing circuitry where necessary. Communication interface 1466 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 1468. In addition, short-range communication may occur, such as using a Bluetooth, low power Bluetooth, Wi-Fi, or other such transceiver (not shown). In addition, GPS (Global Positioning System) receiver module 1480 may provide additional navigation- and location-related wireless data to device 1450, which may be used as appropriate by applications running on device 1450.

Device 1450 may also communicate audibly using audio codec 1460, which may receive spoken information from a user and convert it to usable digital information. Audio codec 1460 may likewise generate audible sound for a user, such as through a speaker, e.g., in a handset of device 1450. Such sound may include sound from voice telephone calls, may include recorded sound (e.g., voice messages, music files, etc.) and may also include sound generated by applications operating on device 1450.

The computing device 1450 may be implemented in a number of different forms, as shown in the figure. For example, it may be implemented as a cellular telephone 1483. It may also be implemented as part of a smart phone 1481, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as modules, programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor, or LED (light emitting diode)) for displaying information to the user and a keyboard and a pointing device (e.g., a mouse or a trackball) by which the user can provide input to the computer. Other kinds of devices can be used to provide for interaction with a user as well. For example, feedback provided to the user can be any form of sensory feedback (e.g., visual feedback, auditory feedback, or tactile feedback), and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

In some implementations, the computing devices depicted in FIG. 14 can include sensors that interface with, or are included in, a HMD 1490. For example, one or more sensors included on computing device 1450 or other computing device depicted in FIG. 14, can provide input to HMD 1490 or in general, provide input to that can be used by the HMD 1490. The sensors can include, but are not limited to, a touchscreen, accelerometers, gyroscopes, pressure sensors, biometric sensors, temperature sensors, humidity sensors, and ambient light sensors. Computing device 1450 (e.g., the HMD 1490) can use the sensors to determine an absolute position and/or a detected rotation of the HMD 1490 that can then be used as input for use by the HMD 1490.

In some implementations, one or more input devices included on, or connected to, the computing device 1450 and/or the HMD 1490 can be used as inputs for use by the HMD 1490. The input devices can include, but are not limited to, a touchscreen, a keyboard, one or more buttons, a trackpad, a touchpad, a pointing device, a mouse, a trackball, a joystick, a camera, a microphone, earphones or buds with input functionality, a gaming controller, or other connectable input device.

In some implementations, one or more output devices included on the computing device 1450, and/or in the HMD 1490, can provide output and/or feedback to a user of the HMD 1490. The output and feedback can be visual, tactical, or audio. The output and/or feedback can include, but is not limited to, rendering a display of the HMD 1490, vibrations, turning on and off or blinking and/or flashing of one or more lights or strobes, sounding an alarm, playing a chime, playing a song, and playing of an audio file. The output devices can include, but are not limited to, vibration motors, vibration coils, piezoelectric devices, electrostatic devices, light emitting diodes (LEDs), strobes, and speakers.

In some implementations, computing device 1450 can be placed within HMD 1490 to create an integrated HMD system. HMD 1490 can include one or more positioning elements that allow for the placement of computing device 1450, such as smart phone 1481, in the appropriate position within HMD 1490. In such implementations, the display of smart phone 1481 can render images using a display of the HMD 1490.

In some implementations, the computing device 1450 may appear as another object in a computer-generated, 3D environment. Interactions by the user with the computing device 1450 (e.g., rotating, shaking, touching a touchscreen, swiping a finger across a touch screen) can be interpreted as interactions with the object in the AR/VR space. As just one example, computing device can be a laser pointer. In such an example, computing device 1450 appears as a virtual laser pointer in the computer-generated, 3D environment. As the user manipulates computing device 1450, the user in the AR/VR space sees movement of the laser pointer. The user receives feedback from interactions with the computing device 1450 in the AR/VR environment on the computing device 1450 or on the HMD 1490.

In some implementations, a computing device 1450 may include a touchscreen. For example, a user can interact with the touchscreen in a particular manner that can mimic what happens on the touchscreen with what happens in a display of the HMD 1490. For example, a user may use a pinching-type motion to zoom content displayed on the touchscreen. This pinching-type motion on the touchscreen can cause information provided in display to be zoomed. In another example, the computing device may be rendered as a virtual book in a computer-generated, 3D environment.

In some implementations, one or more input devices in addition to the computing device (e.g., a mouse, a keyboard) can be rendered in a display of the HMD 1490. The rendered input devices (e.g., the rendered mouse, the rendered keyboard) can be used as rendered in the in the display.

A number of implementations have been described. Nevertheless, it will be understood that various modifications may be made without departing from the spirit and scope of the description and claims.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other implementations are within the scope of the following claims.

Further to the descriptions above, a user is provided with controls allowing the user to make an election as to both if and when systems, programs, devices, networks, or features described herein may enable collection of user information (e.g., information about a user's social network, social actions, or activities, profession, a user's preferences, or a user's current location), and if the user is sent content or communications from a server. In addition, certain data may be treated in one or more ways before it is stored or used, so that user information is removed. For example, a user's identity may be treated so that no user information can be determined for the user, or a user's geographic location may be generalized where location information is obtained (such as to a city, ZIP code, or state level), so that a particular location of a user cannot be determined. Thus, the user may have control over what information is collected about the user, how that information is used, and what information is provided to the user.

The computer system (e.g., computing device) may be configured to wirelessly communicate with a network server over a network via a communication link established with the network server using any known wireless communications technologies and protocols including radio frequency (RF), microwave frequency (MWF), and/or infrared frequency (IRF) wireless communications technologies and protocols adapted for communication over the network.

In accordance with aspects of the disclosure, implementations of various techniques described herein may be implemented in digital electronic circuitry, or in computer hardware, firmware, software, or in combinations of them. Implementations may be implemented as a computer program product (e.g., a computer program tangibly embodied in an information carrier, a machine-readable storage device, a computer-readable medium, a tangible computer-readable medium), for processing by, or to control the operation of, data processing apparatus (e.g., a programmable processor, a computer, or multiple computers). In some implementations, a tangible computer-readable storage medium may be configured to store instructions that when executed cause a processor to perform a process. A computer program, such as the computer program(s) described above, may be written in any form of programming language, including compiled or interpreted languages, and may be deployed in any form, including as a standalone program or as a module, component, subroutine, or other unit suitable for use in a computing environment. A computer program may be deployed to be processed on one computer or on multiple computers at one site or distributed across multiple sites and interconnected by a communication network.

Specific structural and functional details disclosed herein are merely representative for purposes of describing example implementations. Example implementations, however, may be embodied in many alternate forms and should not be construed as limited to only the implementations set forth herein.

The terminology used herein is for the purpose of describing particular implementations only and is not intended to be limiting of the implementations. As used herein, the singular forms "a," "an," and "the" are intended to include the plural forms as well, unless the context clearly indicates otherwise. It will be further understood that the terms "comprises," "comprising," "includes," and/or "including," when used in this specification, specify the presence of the stated features, steps, operations, elements, and/or components, but do not preclude the presence or addition of one or more other features, steps, operations, elements, components, and/or groups thereof.

It will be understood that when an element is referred to as being "coupled," "connected," or "responsive" to, or "on," another element, it can be directly coupled, connected, or responsive to, or on, the other element, or intervening elements may also be present. In contrast, when an element is referred to as being "directly coupled," "directly connected," or "directly responsive" to, or "directly on," another element, there are no intervening elements present. As used herein the term "and/or" includes any and all combinations of one or more of the associated listed items.

Spatially relative terms, such as "beneath," "below," "lower," "above," "upper," and the like, may be used herein for ease of description to describe one element or feature in relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" can encompass both an orientation of above and below. The device may be otherwise oriented (rotated 130 degrees or at other orientations) and the spatially relative descriptors used herein may be interpreted accordingly.

Example implementations of the concepts are described herein with reference to cross-sectional illustrations that are schematic illustrations of idealized implementations (and intermediate structures) of example implementations. As such, variations from the shapes of the illustrations as a result, for example, of manufacturing techniques and/or tolerances, are to be expected. Thus, example implementations of the described concepts should not be construed as limited to the particular shapes of regions illustrated herein but are to include deviations in shapes that result, for example, from manufacturing. Accordingly, the regions illustrated in the figures are schematic in nature and their shapes are not intended to illustrate the actual shape of a region of a device and are not intended to limit the scope of example implementations.

It will be understood that although the terms "first," "second," etc. may be used herein to describe various elements, these elements should not be limited by these terms. These terms are only used to distinguish one element from another. Thus, a "first" element could be termed a "second" element without departing from the teachings of the present implementations.

Unless otherwise defined, the terms (including technical and scientific terms) used herein have the same meaning as commonly understood by one of ordinary skill in the art to which these concepts belong. It will be further understood that terms, such as those defined in commonly used dictionaries, should be interpreted as having a meaning that is consistent with their meaning in the context of the relevant art and/or the present specification and will not be interpreted in an idealized or overly formal sense unless expressly so defined herein.

While certain features of the described implementations have been illustrated as described herein, many modifications, substitutions, changes, and equivalents will now occur to those skilled in the art. It is, therefore, to be understood that the appended claims are intended to cover such modifications and changes as fall within the scope of the implementations. It should be understood that they have been presented by way of example only, not limitation, and various changes in form and details may be made. Any portion of the apparatus and/or methods described herein may be combined in any combination, except mutually exclusive combinations. The implementations described herein can include various combinations and/or sub-combinations of the functions, components, and/or features of the different implementations described.

What is claimed is:

1. A computer program product, the computer program product being tangibly embodied on a non-transitory computer-readable storage medium and comprising instructions that, when executed by at least one computing device, are configured to cause the at least one computing device to:
   store a set of image frames captured during a time interval by a plurality of photodetectors;
   determine a touch event occurring during the time interval and associated with touch surfaces within the set of image frames determined from reflected light captured by the plurality of photodetectors;
   initiate, based on the touch event, generation of biometric data from the touch surfaces;
   determine, for at least one image frame of the set of image frames, a first subset of the plurality of photodetectors associated with a corresponding touch surface;
   determine, from the first subset of the plurality of photodetectors, a second subset of the plurality of photodetectors, including evaluating a signal quality of individual ones of the first subset of the plurality of photodetectors to select the second subset of the plurality of photodetectors as a usable subset for generating the biometric data;
   aggregate detection signals from the reflected light of the touch surfaces, including from the second subset of the plurality of photodetectors, to obtain a time series of aggregated detection signals; and
   generate the biometric data, based on the time series of aggregated detection signals.

2. The computer program product of claim 1, wherein the instructions, when executed, are further configured to cause the at least one computing device to:
   determine the touch event including evaluating whether the set of image frames as a whole provides usable data for generating the biometric data.

3. The computer program product of claim 2, wherein the instructions, when executed, are further configured to cause the at least one computing device to:
   characterize a spatiotemporal smoothness of the touch event.

4. The computer program product of claim 2, wherein the instructions, when executed, are further configured to cause the at least one computing device to:
   characterize a convexity of the corresponding touch surface; and
   determine whether to include the detection signals corresponding to the set of image frames in the time series of aggregated detection signals, based on the convexity.

5. The computer program product of claim 2, wherein the instructions, when executed, are further configured to cause the at least one computing device to:
   perform spectral analysis on the aggregated detection signals of the set of image frames to determine frequency information for the aggregated detection signals; and
   generate the biometric data including a heart rate, using the frequency information.

6. The computer program product of claim 1, wherein the instructions, when executed, are further configured to cause the at least one computing device to:
   perform, for the at least one image frame of the set of image frames, contact binarization for at least one photodetector of the corresponding touch surface, to thereby determine whether to include the at least one photodetector in the second subset of the plurality of photodetectors.

7. The computer program product of claim 1, wherein the instructions, when executed, are further configured to cause the at least one computing device to:
   track movement of the touch surfaces of the touch event across the plurality of photodetectors and during the time interval, wherein the second subset of the plurality of photodetectors includes photodetectors from which the detection signals are obtained during the movement.

8. The computer program product of claim 1, wherein the instructions, when executed, are further configured to cause the at least one computing device to:
determine occurrence of the touch event from the plurality of photodetectors while the plurality of photodetectors are being used for optical finger navigation (OFN).

9. The computer program product of claim 1, wherein the instructions, when executed, are further configured to cause the at least one computing device to:
perform a comparison of the biometric data against stored biometric data; and perform an authentication, based on the comparison.

10. A computer-implemented method, the method comprising:
storing a set of image frames captured during a time interval by a plurality of photodetectors;
determining a touch event occurring during the time interval and associated with touch surfaces within the set of image frames determined from reflected light captured by the plurality of photodetectors;
initiating, based on the touch event, generation of biometric data from the touch surfaces;
determining, for at least one image frame of the set of image frames, a first subset of the plurality of photodetectors associated with a corresponding touch surface;
determining, from the first subset of the plurality of photodetectors, a second subset of the plurality of photodetectors, including evaluating a signal quality of individual ones of the first subset of the plurality of photodetectors to select the second subset of the plurality of photodetectors as a usable subset for generating the biometric data;
aggregating detection signals from the reflected light of the touch surfaces, including from the second subset of the plurality of photodetectors, to obtain a time series of aggregated detection signals; and
generating the biometric data, based on the time series of aggregated detection signals.

11. The method of claim 10, further comprising:
determining the touch event including evaluating whether the set of image frames as a whole provides usable data for generating the biometric data.

12. The method of claim 11, further comprising:
characterizing convexities of the corresponding touch surface of image frames of the set of image frames; and
determining whether to include the detection signals corresponding to the image frames in the time series of aggregated detection signals, based on the convexities.

13. The method of claim 11, further comprising:
performing spectral analysis on the aggregated detection signals of the set of image frames to determine frequency information for the aggregated detection signals; and
generating the biometric data including a heart rate, using the frequency information.

14. The method of claim 10, further comprising:
tracking movement of the touch surfaces of the touch event across the plurality of photodetectors and during the time interval.

15. The method of claim 10, further comprising:
determining occurrence of the touch event from the plurality of photodetectors while the plurality of photodetectors are being used for optical finger navigation (OFN).

16. A computing device comprising:
a processor;
a storage medium storing instructions;
a body;
a light source coupled to the body and configured to generate light; and
a photodetector array including a plurality of photodetectors that is coupled to the body and configured to detect reflected light of the light source;
wherein the instructions, when executed by the processor, cause the computing device to
store a set of image frames captured during a time interval by the photodetector array;
determine a touch event occurring during the time interval and associated with touch surfaces within the set of image frames determined from the reflected light;
initiate, based on the touch event, generation of biometric data from the touch surfaces;
determine, for at least one image frame of the set of image frames, a first subset of the plurality of photodetectors associated with a corresponding touch surface;
determine, from the first subset of the plurality of photodetectors, a second subset of the plurality of photodetectors, including evaluating a signal quality of individual ones of the first subset of the plurality of photodetectors to select the second subset of the plurality of photodetectors as a usable subset for generating the biometric data;
aggregate detection signals from the reflected light of the touch surfaces, including from the second subset of the plurality of photodetectors, to obtain a time series of aggregated detection signals; and
generate the biometric data, based on the time series of aggregated detection signals.

17. The computing device of claim 16, wherein the instructions, when executed by the processor, cause the computing device to:
determine the touch event including evaluating whether the set of image frames as a whole provides usable data for generating the biometric data.

18. The computing device of claim 16, wherein the computing device includes at least one or more of a smartwatch, a ring, smartglasses, or a smartphone.

* * * * *